United States Patent
Bjornson et al.

(10) Patent No.: US 7,341,362 B2
(45) Date of Patent: Mar. 11, 2008

(54) PHOTOACTIVATION DEVICE AND METHOD

(75) Inventors: Torleif Bjornson, Gilroy, CA (US); Hrair Kirakossian, San Jose, CA (US); Albert W. Brown, Jr., San Jose, CA (US); William Wevers, Longmont, CO (US); Hossein Salimi-Moosavi, Sunnyvale, CA (US)

(73) Assignee: Monogram Biosciences, Inc., South San Francisco, CA (US)

( * ) Notice: Subject to any disclaimer, the term of this patent is extended or adjusted under 35 U.S.C. 154(b) by 614 days.

(21) Appl. No.: 10/496,683

(22) PCT Filed: Dec. 18, 2002

(86) PCT No.: PCT/US02/40442

§ 371 (c)(1),
(2), (4) Date: May 26, 2004

(87) PCT Pub. No.: WO03/051669

PCT Pub. Date: Jun. 26, 2003

(65) Prior Publication Data

US 2004/0257808 A1 Dec. 23, 2004

(51) Int. Cl.
*F21V 29/00* (2006.01)
(52) U.S. Cl. .................. 362/294; 362/235; 362/551

(58) Field of Classification Search ............... 362/551, 362/554, 555, 572–573, 580, 582, 294; 433/29
See application file for complete search history.

(56) References Cited

U.S. PATENT DOCUMENTS

| | | | |
|---|---|---|---|
| 4,822,335 A | 4/1989 | Kawai | 604/20 |
| 5,445,608 A | 8/1995 | Chen | 604/20 |
| 5,571,152 A | 11/1996 | Chen | 607/92 |
| 6,200,134 B1 | 3/2001 | Kovac | 433/29 |
| 6,367,949 B1 | 4/2002 | Pederson | 362/240 |
| 6,471,716 B1 | 10/2002 | Pecukonis | 607/89 |
| 6,692,250 B1 * | 2/2004 | Decaudin et al. | 433/29 |
| 7,066,733 B2 * | 6/2006 | Logan et al. | 433/29 |

* cited by examiner

*Primary Examiner*—Ali Alavi
(74) *Attorney, Agent, or Firm*—Stephen C. Macevicz

(57) ABSTRACT

A photoactivation apparatus (200) separately delivers light to a plurality of wells of a multiwell plate (110). The device-includes a plurality of light emitting diodes (210) attached to a first surface of a substrate (220) such that when the photoactivation apparatus is positioned on the multiwell plate each of the light emitting diodes delivers light to one corresponding well. The light emitting diodes (210) may extend at least partially into the wells of the multiwell plate. A heat sink (250) and fan may be provided on the device to dissipate heat generated by the light emitting diodes. The components are preferably enclosed in a conveniently-sized housing (270). The housing may include one or more grips and air vents. The apparatus includes an interlocking lip (230) defining a recess which is sized to receive at least a portion of the multiwell plate. A power supply connected to the apparatus and configured to provide an equal voltage across each of the light emitting diodes.

21 Claims, 4 Drawing Sheets

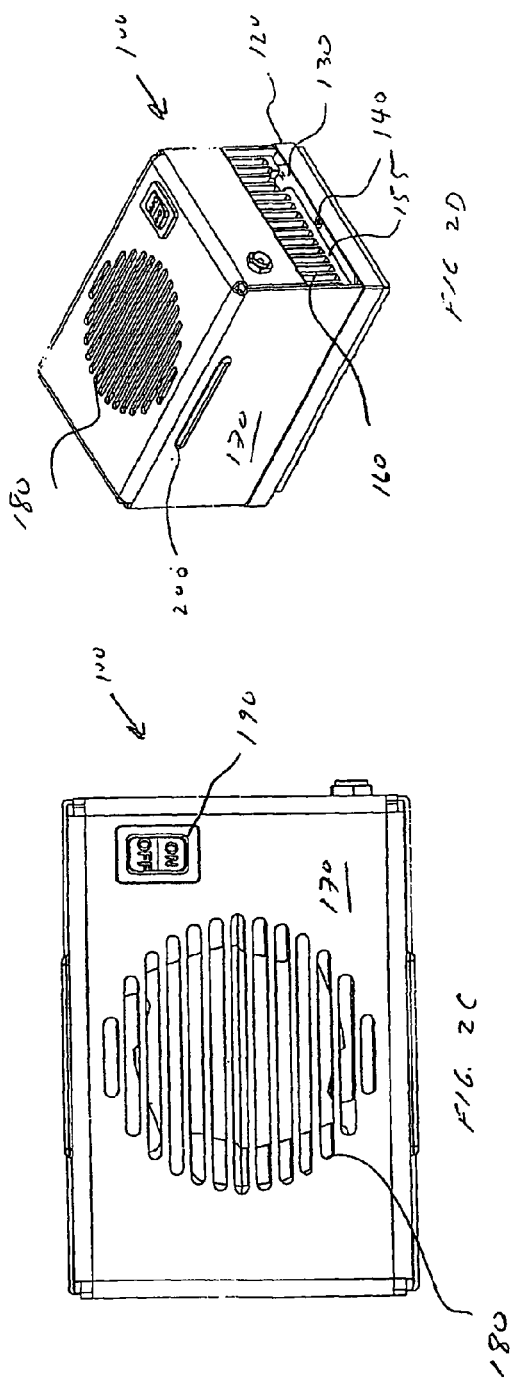
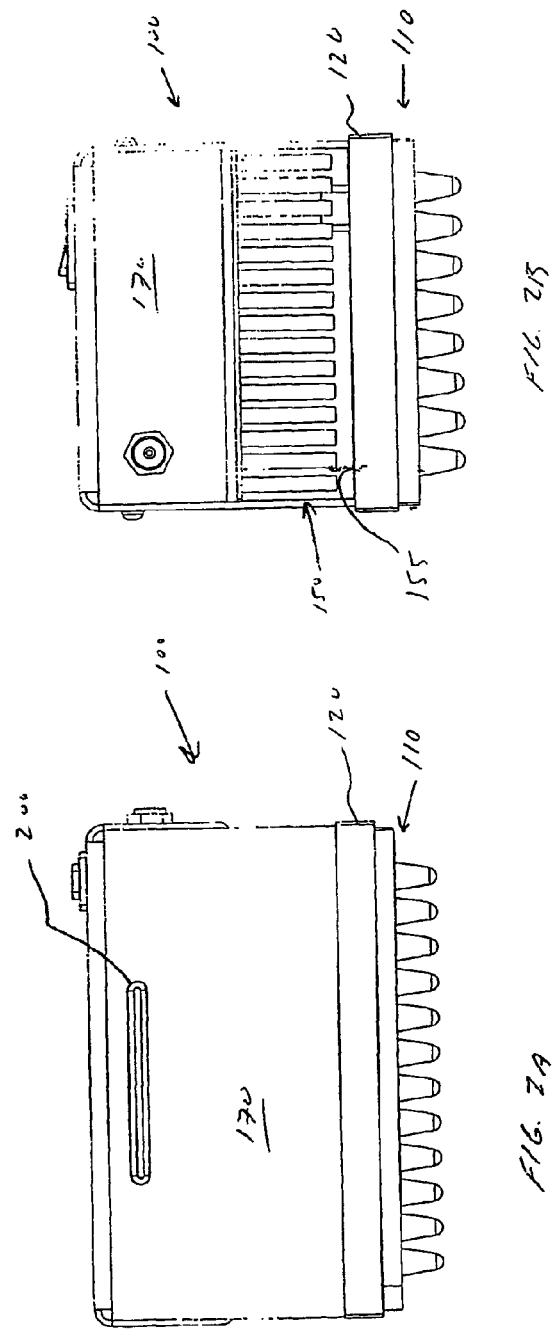

PHOTOACTIVATION DEVICE AND METHOD

TECHNICAL FIELD

This invention is generally related to devices for irradiating photoactive compositions and in particular to devices for irradiating photoactive compositions in a multiwell plate.

BACKGROUND

Photoactivation devices irradiate a target substance, site or compound. They are useful in a variety of areas such as oncology, photography, industrial photocuring, and other commercial applications.

Current medical therapies, for example, use photoactivation devices to irradiate photosensitizers (molecules which can absorb light to produce a chemical reaction which would not occur in their absence). In response to light, photosensitizers catalyze oxidation and/or reduction of certain chemical moieties. Such reactions can be identified in skin diseases of phototoxicity in humans, livestock, and experimental animals; light-activated pesticides; and medical treatments including photochemotherapy and phototherapy of jaundice, herpes simplex and psoriasis. It has been shown that photosensitizers can cause cell death, DNA damage, protein damage, membrane damage, mutagenesis, and tumor destruction. Oncologists capitalize on this phenomena by introducing photosensitizers to tumor sites in localized concentrations. The site is subsequently exposed to light resulting in the generation of singlet oxygen which destroys the cancer cells and vasculature.

Photosensitizer chemistry is also used in genetic, proteomic and other biochemical analysis. See, for example, International Application No. WO 01/83502 demonstrating multiplexed assays using photoactive compounds. These assays are based on releasable labels (e.g. fluorescent, electrochemical, etc,) that are connected to targets or probes by cleavable linkages. By using the sensitizer chemistries to cleave the label, detectable signals are generated which can be used to monitor binding or hybridization events such as antibody/antigen reactions, enzyme/substrate interaction, probe/target hybridization, and protein/receptor binding. For purposes of sample handling and general convenience, it is desirable to conduct these assays in a conventional microtiter or multiwell plate.

Various types of light sources can be used to carry out the above mentioned applications. An example of one light-emitting device which may be used in photocuring and phototherapy applications is disclosed in U.S. Pat. No. 5,634,711 (the '711 patent). In the '711 patent, a hand-held portable light emitting device features an array of light emitting diodes and a tapered optical assembly to direct light from the array of light emitting diodes at a photoreaction site.

U.S. Pat. No. 5,445,608 (the '608 patent) also discloses a light emitting device that can be used in phototherapy applications. In the '608 patent, an implantable probe has an array of light emitting diodes mounted on a bar inside the implantable probe. The probe is normally intended to be implanted inside a patient's body to irradiate a treatment site.

Lamps are also used to irradiate photoactive compounds. Lamps however are bulky and generate unwanted heat. Excess heat can damage the target site or fixture. For example, excess heat can melt (or soften) a sample holding structure such as a multiwell plate in multiplexed assays. Excess heat also can destroy the samples within the wells.

Another drawback of excess heat is that each reaction site (e.g., each well of a multiwell plate) receives an unequal amount of light. That is, there is an uneven distribution of light from well to well because the distance between the light source and each well is different. Consequently, the samples contained within the wells receive an unequal amount of light. A uniform distribution of light is desirable in assays that generate varying results based upon their exposure to light.

None of the above discussed light emitting devices provide for the features and advantages of the present invention as described hereinafter. It is therefore desirable to provide an apparatus and method for uniformly delivering separate light to individual wells such that each sample is separately irradiated. Still other advantages of the present invention will become apparent upon reading the following disclosure in combination with the drawings.

SUMMARY OF THE INVENTION

One variation of the present invention is a photoactivation apparatus for delivering light to a plurality of wells of a multiwell plate. It generally comprises a substrate and a plurality of light emitting elements attached to a first surface of the substrate. The plurality of light emitting elements (e.g., light emitting diodes) are preferably arranged on the first surface such that when the photoactivation apparatus is positioned on the multiwell plate each of the light emitting elements delivers light to one corresponding well. The light emitting elements may extend partially or completely into the wells of the multiwell plate when the apparatus is positioned on the multiwell plate. Also, any number of light emitting elements may be attached to the substrate. In one variation, the apparatus comprises 96 light emitting diodes.

In another variation of the present invention, the photoactivation apparatus includes a heat sink secured to a second surface of the substrate. The heat sink may comprise a base and a plurality of fins extending from the base. The heat sink can be secured to the second surface of the substrate with a thermally conductive adhesive.

In another variation of the present invention, the photoactivation apparatus features a fan facing the heat sink. The fan faces the heat sink such that when the fan is activated, the fan moves air across the heat sink dissipating heat generated by the light emitting diodes. In another variation of the present invention, the heat sink and fan are enclosed in a housing. The housing may further include a lip defining a recess that is sized to receive at least a portion of the multiwell plate when the apparatus is positioned on the multiwell plate.

In another variation of the present invention, the apparatus includes a power supply and the apparatus is configured to provide an equal voltage across each of the light emitting diodes. In another variation of the present invention, the substrate is a PC board having a circuit printed thereon to provide current to each of the light emitting diodes.

Yet another variation of the present invention includes a kit for performing photoactive reactions comprising a photoactivation apparatus as recited above and a multiwell plate wherein the photoactivation apparatus is positioned on the multiwell plate such that each of the plurality of light emitting elements delivers light to a corresponding well to photoactivate compounds contained therein.

Yet another variation of the present invention is a method for uniformly photoactivating a plurality of photoactive chemicals in a plurality of wells of a multiwell plate. The method includes simultaneously irradiating each well of the plurality of wells with separate light. The irradiating step can be performed with a plurality of light emitting diodes wherein the light emitting diodes are located such that each light emitting diode delivers light to one corresponding well. In a variation, the method further comprises dissipating heat generated from the step of irradiating. Heat may be dissipated using a heat sink in thermal connection with the light emitting diodes. Air may also be moved across the heat sink to increase heat dissipation.

BRIEF DESCRIPTION OF THE DRAWINGS

FIG. 2A is a front view of the photoactivation device positioned atop a multiwell plate.

FIGS. 2B, 2C and 2D are side, top and isometric views of the assembly shown in FIG. 2A.

DETAILED DESCRIPTION OF THE INVENTION

This invention is a photoactivation apparatus for irradiating a plurality of samples contained in wells of, for example, a multiwell plate. The photoactivation apparatus includes a plurality of light emitting elements that separately direct light at the samples. In one embodiment, the light emitting elements are arranged such that, when the apparatus is positioned on the multiwell plate, the light emitting elements have a one-to-one correspondence with the wells. That is, one light emitting element irradiates one and only one corresponding well. The photoactivation apparatus of the present invention thus can conveniently provide an equal amount of light to multiple samples contained in separate wells of a multiwell plate. By "positioned on the multiwell plate" it is meant that the apparatus is detachably (or non-detachably) covering, coupled or otherwise attached to the multiwell plate.

Figure 1:
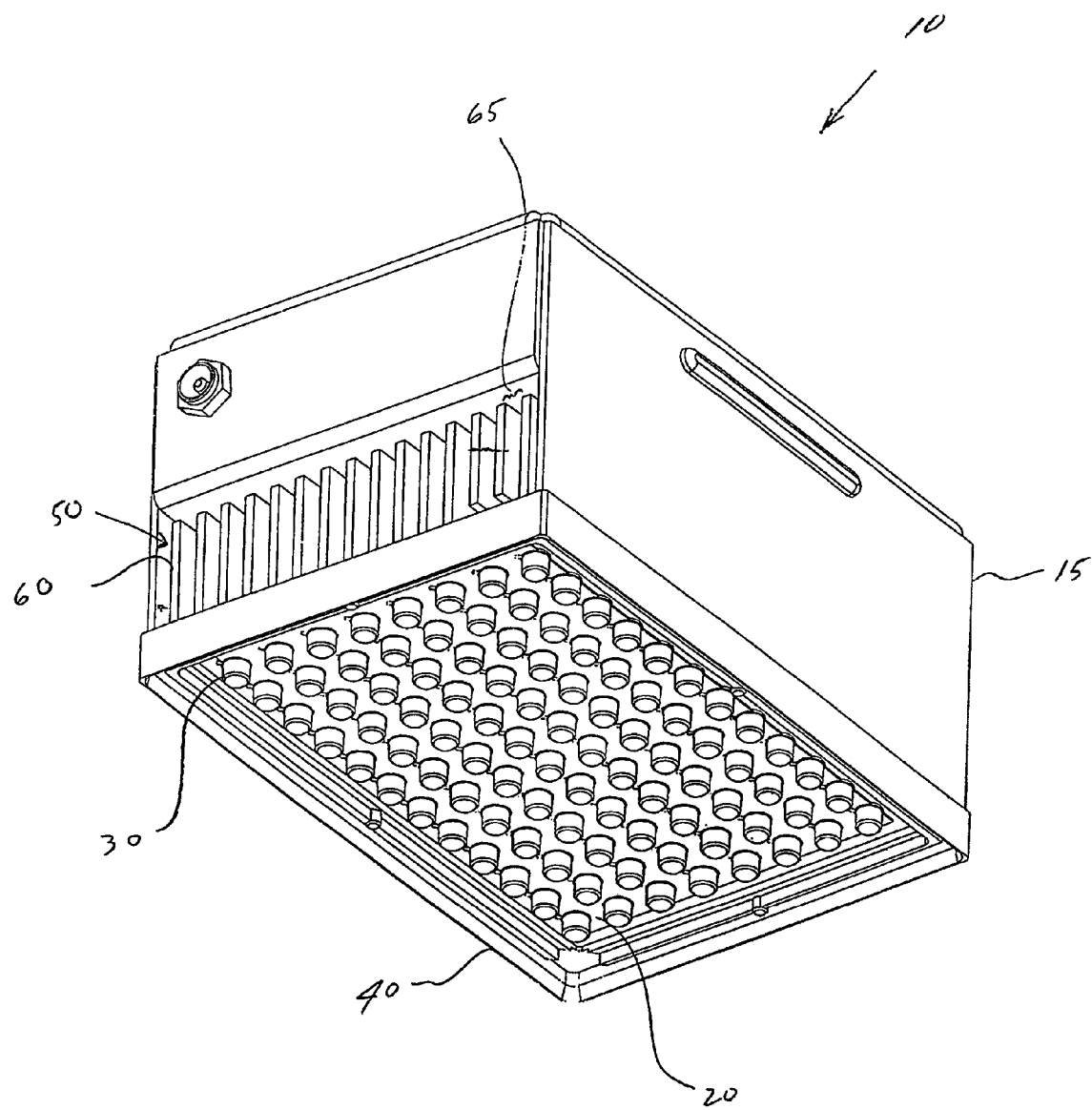
FIG. 1 is a bottom perspective view of a photoactivation device in accordance with the present invention.

Referring to FIG. 1, a photoactivation apparatus or cover 10 is shown. The cover includes a housing 15, substrate 20 and ninety-six light emitting elements 30 secured to the substrate. In one embodiment, the light emitting elements are LEDs. A suitable LED is a high power GaAlAs IR emitter such as model number OD-880W manufactured by OPTO DIODE CORP, Newbury Park, Calif., USA. However, other types of light emitting elements may be used in accordance with the present invention. For example, optical fibers may be incorporated into the cover to deliver selected wavelengths of light to individual wells.

Also shown in FIG. 1 is thermally conductive heat sink 50. Heat sink 50 may be any thermally conductive material such as aluminum. Heat sink 50 is shown having sixteen fins 60 and gaps 65 separating the fins. While sixteen fins are shown in this embodiment, the heat sink may include more or less fins depending on the amount of heat to be dissipated. Generally, fins are added to increase the surface area which results in more heat being dissipated. Example dimensions for the fin height and width respectively are 0.8 to 1.0 in. and 0.05 to 0.15 in. and more preferably, 0.9 in. and 0.1 in respectively. Consequently, the gaps are about 0.09 to 0.20 in.

The heat sink 50 is desirably secured to the substrate 20 flush in order to minimize any spaces formed therebetween. Spaces and micro spaces containing air decrease the thermal conduction efficiency at this joint and are therefore undesirable. Thermal fillers may be disposed between the heat sink and the substrate to ensure adequate heat transfer. For example, Sil-Pad® (manufactured by The Bergquist Company, Chanhassen, Minn. 55317) can join the heat sink with the substrate. However, other thermal gap fillers, tapes and compounds may be applied to thermally connect the components as is known to those of skill in the art. Also, suitable materials for the substrate include rigid polymers such as Emerson & Cumming, EcoBond™ 285 thermally conductive epoxy adhesive and PC board.

In one embodiment, a fan (not shown) is positioned within housing 15. The fan should face the heat sink 50. This arrangement increases heat transfer efficiency by forcing a coolant (e.g., air) across the fins. Preferably, the fan has a rating of 20 to 33 cubic feet per minute to ensure adequate heat dissipation. A suitable fan is ComAir Rotron™ FS05H3. Of course other heat sink designs may be employed as is known to those of skill in the art.

It has been found that the above described configuration is suitable for maintaining an operating temperature measured at the substrate to within 40 degrees Celsius of a predetermined temperature. For example, it has been found that the above described configuration maintains an operating temperature at about 30-40 degrees Celsius. Consequently, the wavelength of the LEDs may remain constant; the multiwell plate does not soften or melt; and the samples do not become denatured, destroyed or otherwise adversely affected.

The dimensions and shape of the photoactivating cover of the present invention may vary widely. It is preferred, however, that the cover has dimensions suitable to fit atop a multiwell plate 100 as shown in FIGS. 2A-2D. For example, in one embodiment the cover has dimensions to fit atop a multiwell plate such as a MicroAmp™ plate (part no.: N801-0560) from ABI. In another embodiment, the cover has an overall size and mass such that it is capable of being hand held and manipulated.

Referring to FIGS. 2A-2D, the photoactivation cover 100 of the present invention is sized to fit (or cover) a liquid containment structure or multiwell plate 110. The cover preferably includes a lip 120 that extends from the cover 100. The lip 120 includes a cavity or recess (not shown) which is sized to receive a portion of well plate 110. In one embodiment, the lip cavity forms a snap or interference fit with the well plate. Lip 120 may be polymer, metal or metal alloy. Various polymers can be used such as, for example, polyethylene, polycarbonate, polystyrene, or acrylics.

FIG. 2D shows an isometric view of cover 100 having lip 120. A substrate 130 is secured to lip 120 with a fastener such as a screw 140. However, other fasteners and securing techniques may be utilized to carry out the present invention.

A heat sink 150 is attached to substrate 130. The heat sink includes a base 155 and fins 160. A thermally conductive compound is preferably applied to the joint between the heat sink and the substrate (or card) to ensure efficient thermal conduction between the components. However, a thermal compound is not necessary and the cover of the present invention may operate without a thermal compound and without a heat sink.

In FIG. 2D housing 170 partially encloses heat sink 150 and other components. The housing 170 may include air vents 180. Air vents 180 provide openings for air to enter the housing and flow therethrough. As air flows through the enclosure and across fins 160, heat is dissipated.

Housing 170 also preferably includes a power switch 190. Switch 190 may be designed to turn the photoactive cover on or off by connecting the fan and LEDs with a power supply. Housing may also include a handle 200 to facilitate handling of the device. Of course other vent, switch and handle designs may be incorporated into the cover and be in accordance with the present invention.

Figure 3:
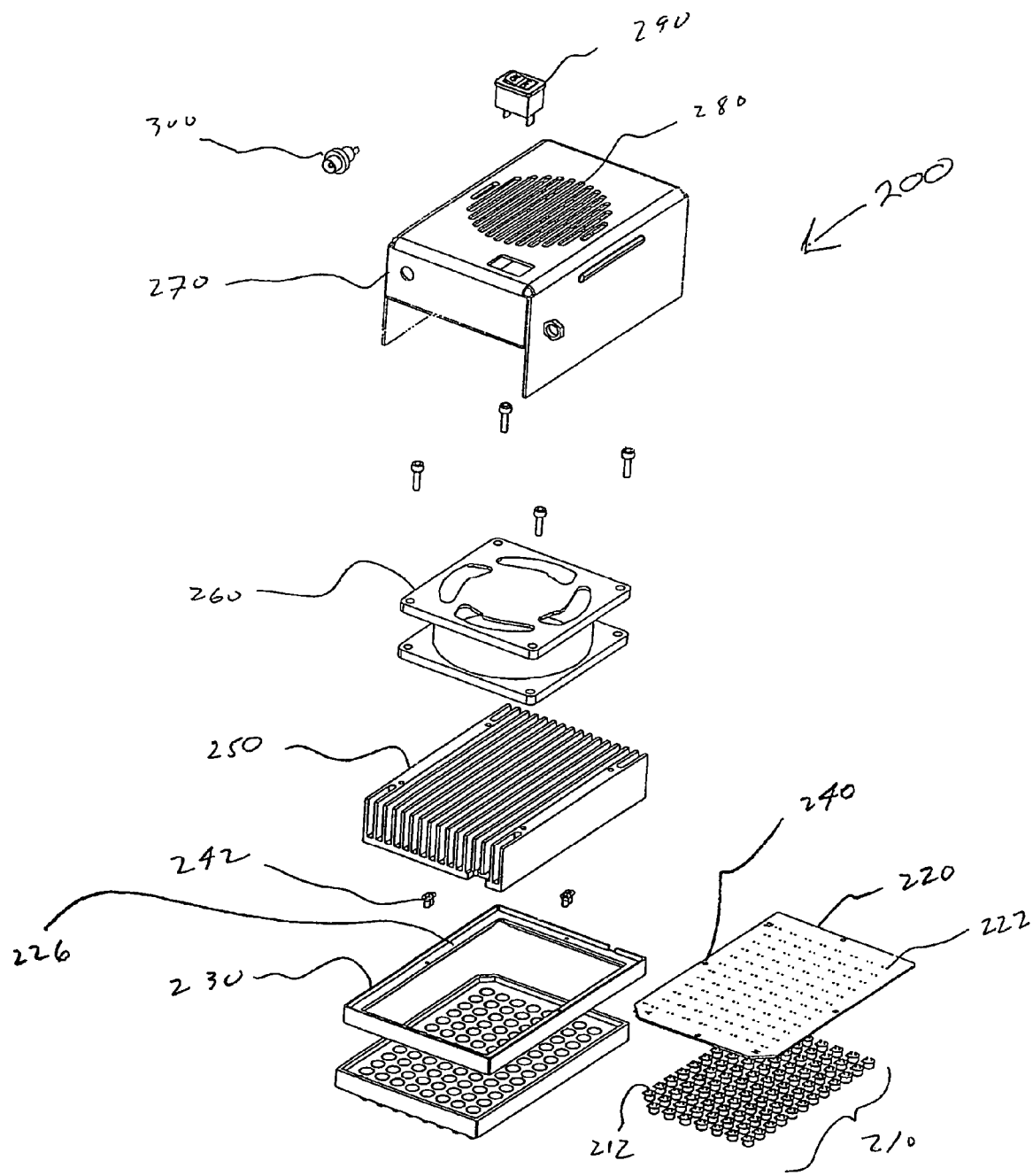
FIG. 3 is an exploded view of the assembly shown in FIG. 2A.

An exploded view of a photoactive cover 200 in accordance with the present invention is shown in FIG. 3. This view is illustrative of the assembly of the present invention. In particular, FIG. 3 shows an array of LEDs 210 to be mounted on PC board 220. The LEDs have leads 212 which are positioned in lead openings 222 of PC board 220 when assembled. Solder is then applied to the leads such that electrical contact is made between the leads and an electrical circuit printed on the substrate.

Once the LEDs are mounted to a first surface of the substrate, the substrate may be mounted to a ledge 226 of lip 230. Screw openings 240 may be provided in the substrate 220 allowing for fasteners such as screws 242 to be inserted therethrough. Screw apertures may also be provided in ledge 226 for receiving screws 242 thereby securing the substrate to the lip.

In this embodiment a heat sink 250 is attached to a surface of the substrate 220 opposite the surface upon which the LEDs are mounted. The heat sink 250 is secured using, for example, a thermally conducting adhesive compound or tape. Heat sink 250 includes fins to provide for increased heat dissipation when air flows therethrough.

FIG. 3 also shows fan 260 to be mounted on top of heat sink 250. The fan 260 may be mounted using screws or other means. A housing 270 at least partially encloses the above mentioned components. The housing 270 includes air vents 280 so that air is drawn through the air vents and across the heat sink.

A power switch 290 and electrical connector 300 are also shown in FIG. 3. The power switch and electrical connector provide power to the apparatus enabling the LEDs to emit light and the fan to displace air.

Figure 4A:
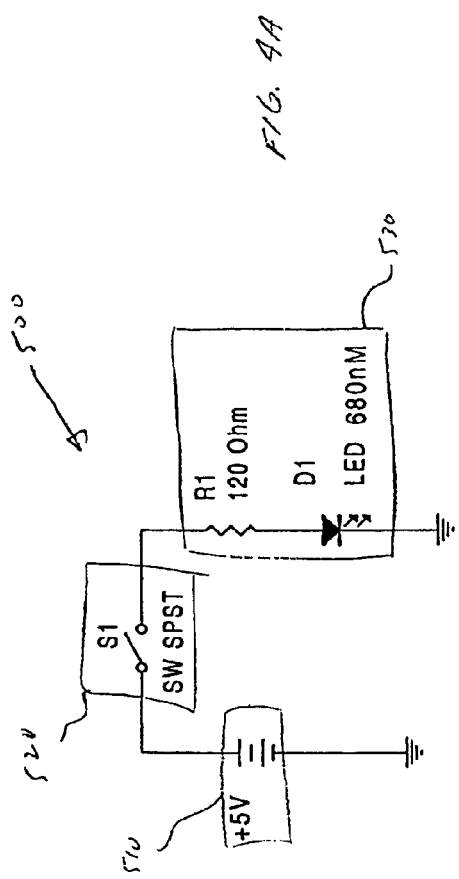
FIG. 4A is a block diagram of a circuit in accordance with one aspect of the present invention having one LED.
Figure 4B:
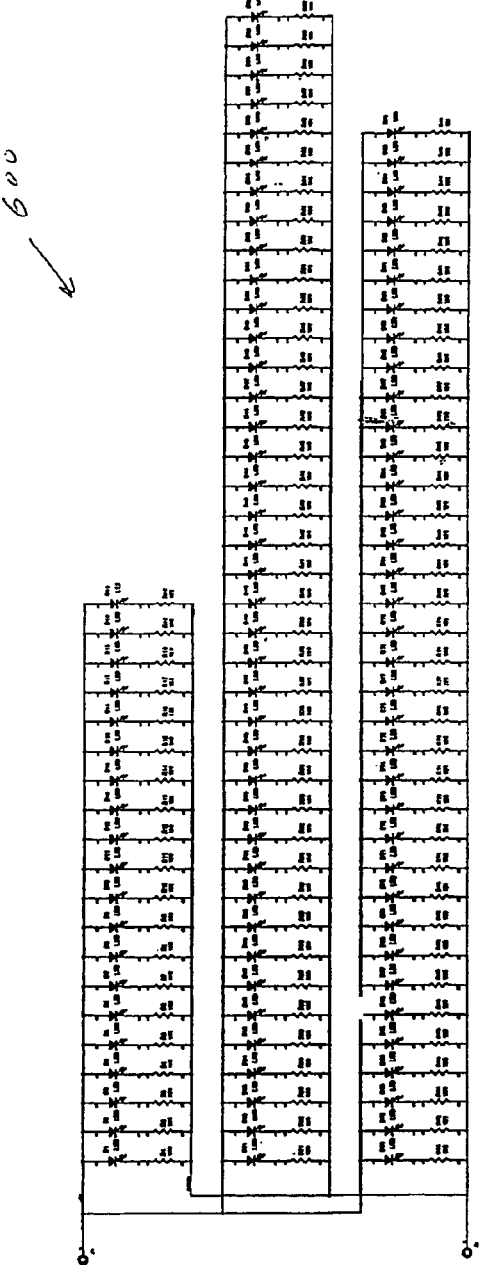
FIG. 4B is an electrical schematic of an array of 96 LEDs in accordance with the present invention.

An electrical block diagram of one circuit configuration 500 of the present invention is shown in FIG. 4A. According to FIG. 4A, a power supply 510 is connected with switch 520. An LED 530 is connected downstream of switch 520 such that when the switch is activated, LED emits light. This circuit 500 shows only one LED. However, the invention may include an array of LEDs preferably electrically connected in parallel. For example, an LED array 600 may be electrically connected as shown in FIG. 4B. Also, a fan is preferably connected between the LED(S) and switch 520 so that when the switch is turned on, the fan and the LEDs are activated. Other electrical circuits may be used to carry out the present invention as is known to those of ordinary skill in the art.

Table 1 shows power data from an array of LEDs arranged as described above. About 25 mA of input current was delivered to each LED. The LEDs. were manufactured by OPTO DIODE CORP., Newbury Park, Calif.

As indicated in Table 1, the measured power for each LED is substantially equal. The overall average power for all LEDs was 2.05 mW with a standard deviation of 0.13 mW. Given that the amount of light delivered from each LED is related to the amount of power of each LED, this data indicates that an equal amount of light is being delivered from each LED. Accordingly, the LED array of the present invention can deliver substantially uniform light from each of the LEDs of the LED array.

TABLE 1

MEASURED POWER FOR LEDS
25 mA input current/LED
100 mW Scale
Zero = 0.2

| | | | | | | | | | | | | | AVE | SD | CV |
|---|---|---|---|---|---|---|---|---|---|---|---|---|---|---|---|
| | 2.1 | 2.1 | 1.9 | 1.9 | 2.1 | 1.8 | 2.2 | 2.0 | 2.0 | 2.3 | 2.0 | 1.9 | 2.03 | 0.14 | 7.02 |
| | 2.0 | 1.9 | 2.2 | 1.8 | 2.0 | 2.0 | 2.2 | 2.2 | 2.0 | 1.9 | 2.2 | 2.0 | 2.03 | 0.14 | 6.74 |
| | 2.1 | 2.2 | 2.1 | 1.9 | 2.1 | 2.2 | 2.1 | 1.9 | 1.9 | 2.0 | 2.3 | 1.9 | 2.06 | 0.14 | 6.70 |
| | 2.0 | 2.0 | 2.1 | 1.9 | 2.2 | 2.0 | 2.1 | 2.0 | 2.1 | 2.1 | 2.0 | 2.1 | 2.05 | 0.08 | 3.89 |
| | 1.8 | 1.9 | 2.2 | 1.9 | 1.9 | 1.7 | 2.2 | 2.0 | 2.0 | 2.2 | 2.2 | 2.1 | 2.01 | 0.17 | 8.61 |
| | 2.1 | 2.0 | 2.2 | 2.1 | 1.9 | 2.0 | 2.1 | 2.2 | 2.1 | 2.2 | 2.1 | 2.0 | 2.08 | 0.09 | 4.50 |
| | 1.9 | 2.0 | 2.1 | 2.0 | 2.2 | 2.2 | 2.0 | 2.2 | 2.1 | 2.3 | 2.1 | 2.1 | 2.10 | 0.11 | 5.37 |
| | 2.2 | 2.1 | 1.9 | 2.0 | 2.2 | 2.1 | 2.1 | 2.3 | 2.0 | 2.0 | 2.1 | 1.8 | 2.07 | 0.14 | 6.63 |
| AVE | 2.03 | 2.03 | 2.09 | 1.94 | 2.08 | 2.00 | 2.13 | 2.10 | 2.03 | 2.13 | 2.13 | 1.99 | | | |
| SD | 0.13 | 0.10 | 0.12 | 0.09 | 0.13 | 0.18 | 0.07 | 0.14 | 0.07 | 0.15 | 0.10 | 0.11 | | | |
| CV | 6.33 | 5.11 | 5.97 | 4.73 | 6.18 | 8.86 | 3.33 | 6.73 | 3.49 | 7.00 | 4.87 | 5.67 | | | |

Average(AVE)           2.05
Standard Deviation (SD)  0.13
CV                      6.24

All publications, patent applications, patents, and other references mentioned herein are incorporated by reference in their entirety. To the extent there is a conflict in a meaning of a term, or otherwise, the present application will control.

All of the features disclosed in the specification (including any accompanying claims, abstract and drawings), and/or all of the steps of any method or process disclosed, may be combined in any combination, except combinations where at least some of such features and/or steps are mutually exclusive. Each feature disclosed, in this specification (including any accompanying claims, abstract and drawings), may be replaced by alternative features serving the same, equivalent or similar purpose, unless expressly stated otherwise. The invention is not restricted to the details of the foregoing embodiments. The invention extends to any novel one, or any novel combination, of the features disclosed in this specification (including any accompanying claims, abstract and drawings), or to any novel one, or any novel combination, of the steps of any method or process so disclosed.

The invention claimed is:

1. A photoactivation apparatus for delivering light to a plurality of wells of a multiwell plate, said apparatus comprising: a substrate having a first surface and a second surface opposite said first surface; and a plurality of light emitting elements attached to said first surface of said substrate, said plurality of light emitting elements arranged on said first surface such that when said photoactivation apparatus is positioned on said multiwell plate each of said light emitting elements delivers light to one corresponding well, and wherein said light emitting elements extend at least partially into said wells when said apparatus is positioned on said multiwell plate.

2. The apparatus of claim 1 further comprising a heat sink secured to said second surface of said substrate, said heat sink comprising a base and a plurality of fins extending from said base.

3. The apparatus of claim 2 wherein said heat sink is secured to said second surface of said substrate with a thermally conductive adhesive.

4. The apparatus of claim 2 further comprising a fan facing said heat sink such that when said fan is on, said fan moves air across said heat sink.

5. The apparatus of claim 4 further comprising a lip having a recess that receives at least a portion of said multiwell plate when said apparatus is positioned on said multiwell plate.

6. The apparatus of any one of the above claims wherein each of said light emitting elements is a light emitting diode.

7. The apparatus of claim 6 further comprising a power supply, said apparatus configured to provide substantially equal power to each of said light emitting diodes to deliver substantially uniform light to said plurality of wells.

8. The apparatus of claim 7 wherein said substrate is a PC board having a circuit printed theron to provide current to each of said light emitting diodes.

9. The apparatus of claim 5 further comprising a housing enclosing said fan and heat sink, said housing further having one or more openings for air to flow through.

10. The apparatus of claim 1 comprising 96 light emitting diodes.

11. A kit for performing photoactive reactions comprising: a photoactivation apparatus as recited in claim 1; and a multiwell plate wherein said photoactivation apparatus is positioned on said multiwell plate such that each of said plurality of light emitting elements delivers light to a corresponding well to photoactivate compounds contained therein.

12. The kit of claim 11 wherein said light emitting elements are light emitting diodes.

13. The kit of claim 12 wherein said apparatus comprises a heat sink in thermal connection to said plurality of light emitting diodes for dissipating heat generated when said light emitting diodes are delivering light.

14. The kit of claim 13 wherein said apparatus further comprises a fan facing said heat sink such that when said fan is activated, said fan moves air across said heat sink.

15. A method for photoactivating a plurality of photoactive chemicals in a plurality of wells of a multiwell plate, said method comprising: simultaneously irradiating each well of said plurality of wells with separate light.

16. The method of claim 15 wherein said irradiating is performed with a plurality of light emitting diodes wherein the light emitting diodes are located such that each of said light emitting diodes delivers light to one corresponding well.

17. The method of claim 16 wherein said multiwell plate includes 96 wells and said irradiating is carried out using 96 light emitting diodes.

18. The method of claim 16 wherein said light emitting diodes extend at least partially into said wells when said apparatus is positioned on said multiwell plate.

19. The method of claim 16 further comprising dissipating heat generated from said irradiating.

20. The method of claim 19 wherein said dissipating heat is performed by providing a heat sink in thermal connection with said light emitting diodes.

21. The method of claim 20 wherein said dissipating heat further comprises moving air across said heat sink.

* * * * *